(12) United States Patent
Rowe (10) Patent No.: US 10,456,282 B2
(45) Date of Patent: Oct. 29, 2019

(54) DELIVERY SYSTEM FOR ANCHOR AND METHOD

(71) Applicant: Medtronic Vascular, Inc., Santa Rosa, CA (US)

(72) Inventor: Travis Rowe, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 120 days.

(21) Appl. No.: 15/480,778

(22) Filed: Apr. 6, 2017

(65) Prior Publication Data
US 2018/0289518 A1  Oct. 11, 2018

(51) Int. Cl.
*A61F 2/95* (2013.01)
*A61F 2/82* (2013.01)
*A61B 17/064* (2006.01)
*A61B 17/068* (2006.01)
*A61F 2/07* (2013.01)

(52) U.S. Cl.
CPC ............ *A61F 2/95* (2013.01); *A61B 17/068* (2013.01); *A61B 17/0644* (2013.01); *A61F 2/82* (2013.01); *A61B 2017/0645* (2013.01); *A61B 2017/0649* (2013.01); *A61F 2/07* (2013.01); *A61F 2220/0016* (2013.01); *A61F 2230/0067* (2013.01); *A61F 2250/0098* (2013.01)

(58) Field of Classification Search
CPC ............... A61F 2/95; A61F 2220/0016; A61F 2220/0008; A61F 2/2442–2/2493; A61B 17/10; A61B 17/00234; A61B 17/122–17/1285; A61B 17/12; A61B 17/0644; A61B 17/0645; A61B 2017/0649; A61B 2017/0498

USPC .................. 606/104; 623/1.11, 1.36
See application file for complete search history.

(56) References Cited

U.S. PATENT DOCUMENTS

| | | | | |
|---|---|---|---|---|
| 4,669,473 A | * | 6/1987 | Richards | A61B 17/0401 606/215 |
| 5,582,616 A | * | 12/1996 | Bolduc | A61B 17/064 606/139 |
| 5,865,791 A | * | 2/1999 | Whayne | A61B 17/00234 604/500 |
| 5,964,772 A | | 10/1999 | Bolduc et al. | |
| 6,293,906 B1 | * | 9/2001 | Vanden Hoek | A61F 2/2481 600/16 |

(Continued)

OTHER PUBLICATIONS

Invitation to Pay Additional Fees, Application No. PCT/US2018/024762, dated Sep. 13, 2018, pp. 1-15.

*Primary Examiner* — Shaun L David
*Assistant Examiner* — Brigid K Byrd (57) ABSTRACT

In accordance with one embodiment, a helical anchor is provided in a relaxed state. During deployment, a distal portion of the helical anchor is superelastically deformed to protrude longitudinally. The longitudinally protruding distal portion of the helical anchor is longitudinally advanced to cause the distal portion to pierce a prosthesis and a vessel wall. The distal portion returns to the relaxed state after passing through the prosthesis and the vessel wall. By superelastically deforming the distal portion during deployment, it is easier to cause the anchor to penetrate the prosthesis and the vessel wall. Further, by having the anchor return to its relaxed state after passing through the prosthesis and vessel wall, better clamping of the prosthesis to the vessel wall is achieved.

20 Claims, 12 Drawing Sheets

(56) References Cited

U.S. PATENT DOCUMENTS

| | | | | |
|---|---|---|---|---|
| 6,607,555 B2* | 8/2003 | Patterson | ............. | A61B 17/064 |
| | | | | 604/95.04 |
| 7,131,979 B2* | 11/2006 | DiCarlo | ............. | A61B 17/0469 |
| | | | | 606/144 |
| 8,162,958 B2* | 4/2012 | Takahashi | ............ | A61B 17/064 |
| | | | | 606/139 |
| 8,968,336 B2* | 3/2015 | Conklin | ............... | A61B 17/068 |
| | | | | 606/142 |
| 9,700,304 B2* | 7/2017 | Koziczynski | .......... | A61B 17/06 |
| 2005/0187568 A1* | 8/2005 | Klenk | ................ | A61B 17/0057 |
| | | | | 606/153 |
| 2006/0258909 A1* | 11/2006 | Saadat | ............... | A61B 1/00142 |
| | | | | 600/121 |
| 2007/0021753 A1* | 1/2007 | Bolduc | ................ | A61B 17/064 |
| | | | | 606/104 |
| 2008/0228255 A1* | 9/2008 | Rust | .......................... | A61F 2/95 |
| | | | | 623/1.11 |
| 2009/0118825 A1* | 5/2009 | Rourke | ................. | A61F 2/2451 |
| | | | | 623/2.11 |
| 2012/0160896 A1 | 6/2012 | Houard | | |
| 2014/0200398 A1* | 7/2014 | Hawkins | ............ | A61B 17/0469 |
| | | | | 600/37 |
| 2014/0379074 A1* | 12/2014 | Spence | ................. | A61F 2/2409 |
| | | | | 623/2.11 |
| 2015/0230802 A1* | 8/2015 | Lagodzki | ......... | A61B 17/12109 |
| | | | | 606/200 |
| 2015/0351912 A1 | 12/2015 | Konstantino et al. | | |
| 2016/0184117 A1* | 6/2016 | Vad | ........................... | A61F 2/95 |
| | | | | 623/1.11 |
| 2017/0086814 A1* | 3/2017 | Howard | ............. | A61B 17/0401 |

* cited by examiner

DELIVERY SYSTEM FOR ANCHOR AND METHOD

BACKGROUND

Field

The present application relates to an intra-vascular device and method. More particularly, the present application relates to a device for treatment of intra-vascular diseases.

Description of the Related Art

A conventional stent-graft typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

To prevent migration of the stent-graft, the stent-graft is anchored to the vessel wall using anchors. Challenges occur in penetrating the stent graft and the vessel wall with the anchors. For example, in certain circumstances, it is difficult to deploy the anchor normal to the stent graft and/or vessel wall due to the tight geometry of the vessel or it is difficult to pierce with a screw motion of the anchor.

SUMMARY

In accordance with one embodiment, a helical anchor is provided in a relaxed state. During deployment, a distal portion of the helical anchor is superelastically deformed to protrude longitudinally. The longitudinally protruding distal portion of the helical anchor is longitudinally advanced to cause the distal portion to pierce a prosthesis and a vessel wall. The distal portion returns to the relaxed state after passing through the prosthesis and the vessel wall. By superelastically deforming the distal portion during deployment, it is easier to cause the anchor to penetrate the prosthesis and the vessel wall. Further, by having the anchor return to its relaxed state after passing through the prosthesis and vessel wall, better clamping of the prosthesis to the vessel wall is achieved.

BRIEF DESCRIPTION OF DRAWINGS

Common reference numerals are used throughout the drawings and detailed description to indicate like elements.

DETAILED DESCRIPTION

Figure 7:
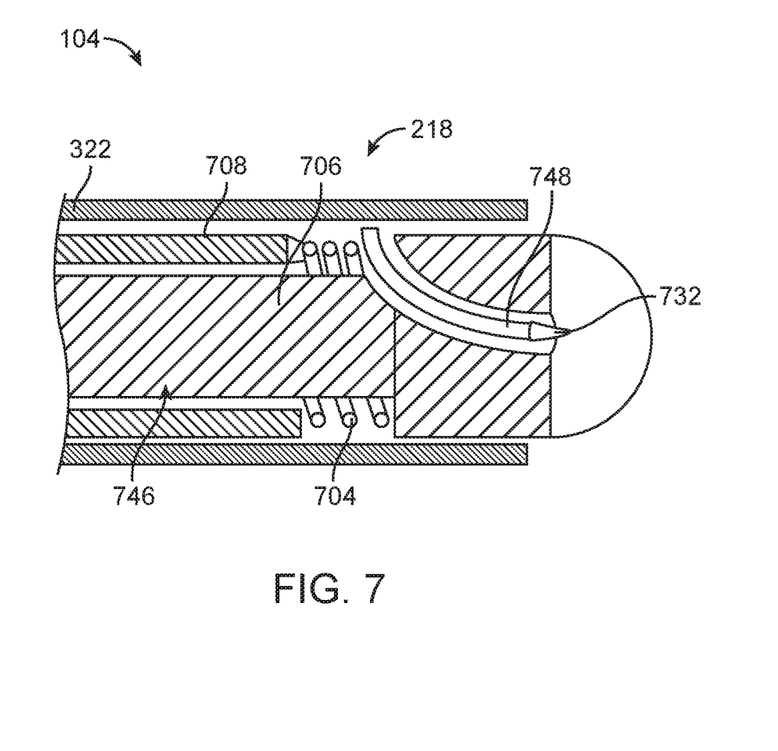
FIG. 7 is a cross-section view of the distal end of the anchor delivery system of FIGS. 1-5 in accordance with one embodiment.
Figure 12:
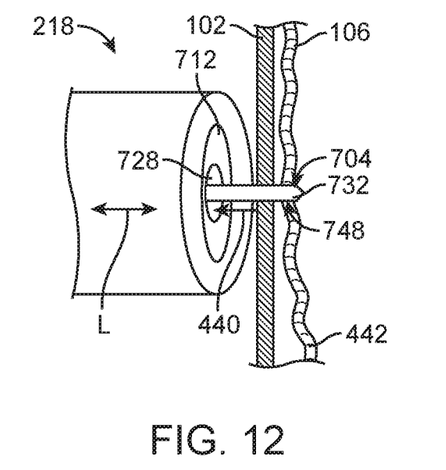
FIG. 12 is a partial cross-sectional view of the anchor during deployment in accordance with one embodiment.

As an overview and in accordance with one embodiment, referring to FIGS. 7 and 12 together, a helical anchor 704 is provided in a relaxed state. During deployment, a distal portion 748 of anchor 704 is superelastically deformed to protrude longitudinally. The longitudinally protruding distal portion 748 of anchor 704 is longitudinally advanced to cause distal portion 748 to pierce a prosthesis 102 and a vessel wall 442.

Figure 13:
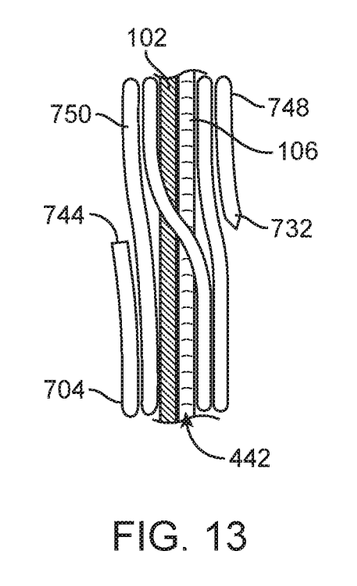
FIG. 13 is a partial cross-sectional view of the final deployed state of the anchor in accordance with one embodiment.

Referring now to FIG. 13, distal portion 748 returns to the relaxed state after passing through prosthesis 102 and vessel wall 442. By superelastically deforming distal portion 748 during deployment, it is easier to cause anchor 704 to penetrate prosthesis 102 and vessel wall 442. Further, by having anchor 704 return to its relaxed state after passing through prosthesis 102 and vessel wall 442, better clamping of prosthesis 102 to vessel wall 442 is achieved.

Figure 1:
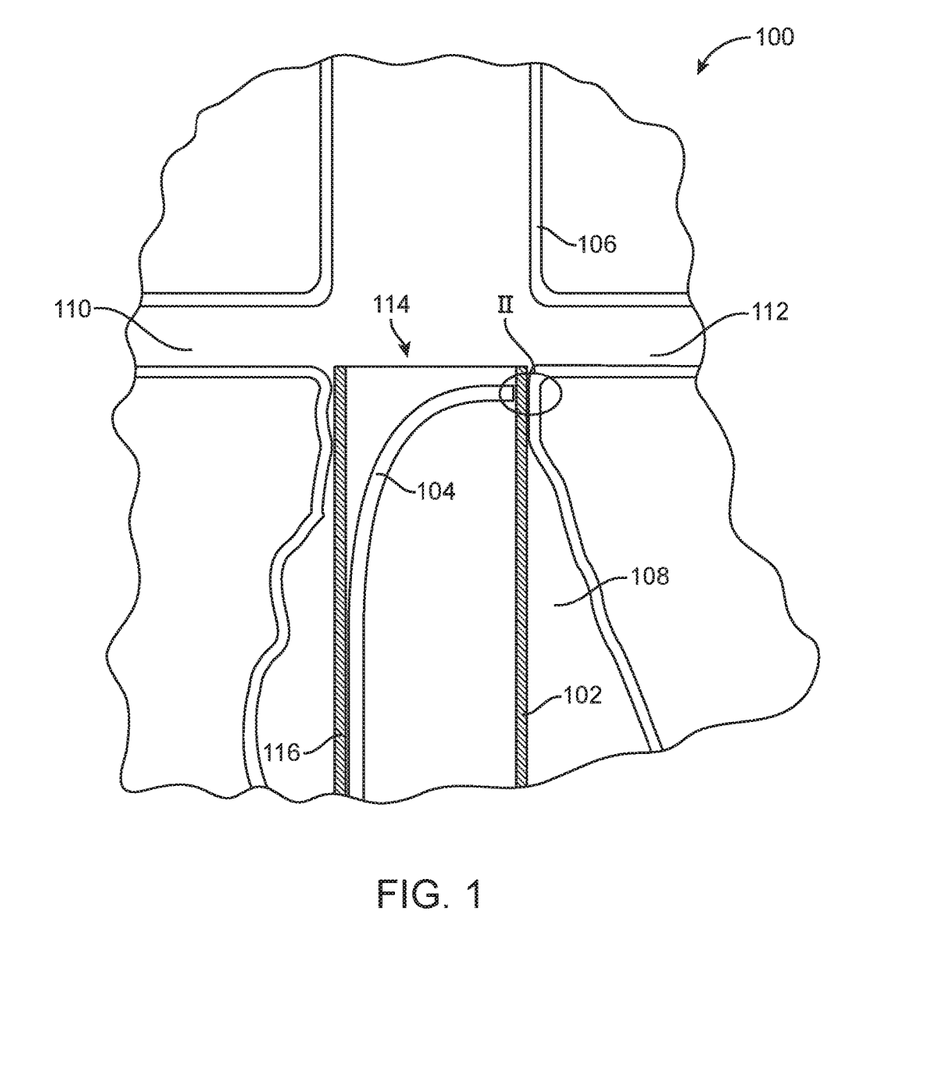
FIG. 1 is a partial cross-sectional view of a vessel assembly including an aneurysm exclusion stent-graft and an anchor delivery system in accordance with one embodiment.

Now in more detail, FIG. 1 is a partial cross-sectional view of a vessel assembly 100 including an aneurysm exclusion stent-graft 102 and an anchor delivery system 104 in accordance with one embodiment. Referring now to FIG. 1, a primary vessel 106, e.g., the aorta, includes an aneurysm 108.

Emanating from primary vessel 106 is a first branch vessel 110 and a second branch vessel 112, sometimes called visceral branches of the abdominal aorta. The location of branch vessels 110, 112 vary from patient to patient. Examples of branch vessels 110, 112 include the renal arteries (RA).

Aneurysm exclusion stent-graft 102 is deployed into primary vessel 106 to exclude aneurysm 108 using any one of a number of techniques well known to those of skill in the art. Aneurysm exclusion stent-graft 102 is deployed distal to branch vessels 110, 112 and thus exposes and maintains perfusion of branch vessels 110, 112. In other embodiments, aneurysm exclusion stent-graft 102 covers one or more of branch vessels 110, 112 and has openings and or other structures to maintain perfusion of branch vessels 110, 112. In either embodiment, once anchored within primary vessel 106, blood flows through a lumen 114 of aneurysm exclusion stent-graft 102 thus excluding aneurysm 108.

In one embodiment, aneurysm exclusion stent-graft 102 includes graft material 116 and one or more stents. Although one example of aneurysm exclusion stent-graft 102 is described, in other embodiments, other prostheses are deployed depending upon the particular application.

In one embodiment, aneurysm exclusion stent-graft 102 must be anchored to primary vessel 106 to prevent migration of aneurysm exclusion stent-graft 102. For example, aneurysm 108 is a short neck aneurysm having little to no healthy tissue between branch vessels 110, 112 and aneurysm 108. Accordingly, aneurysm exclusion stent-graft 102 is anchored to primary vessel 106 as described below.

Figure 2:
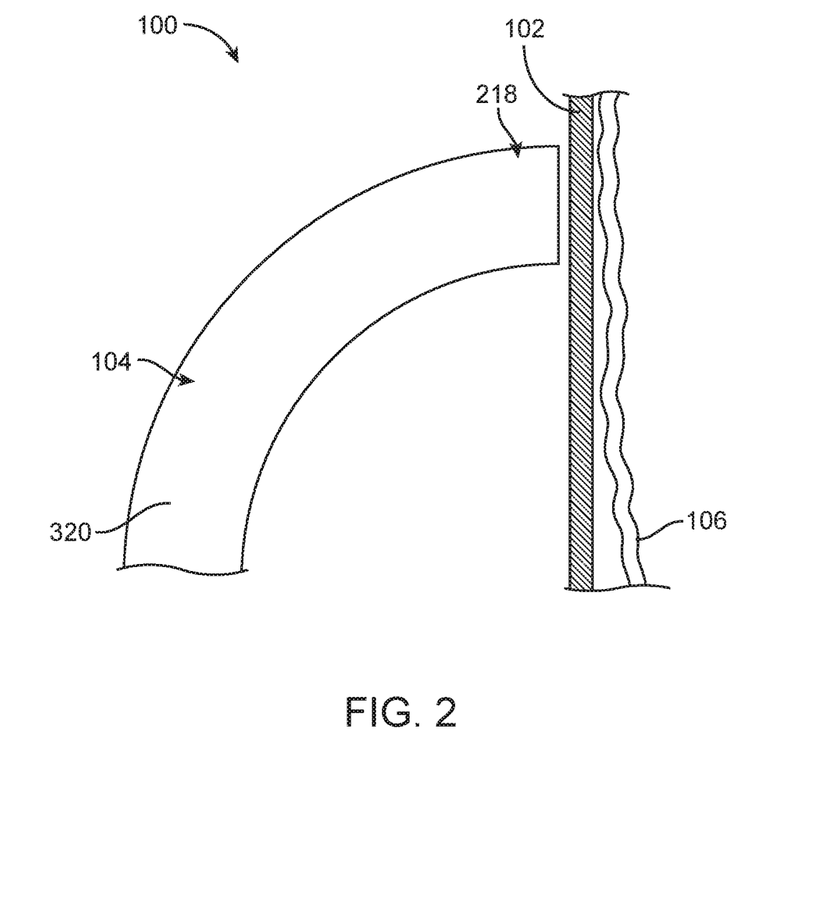
FIG. 2 is an enlarged side view of a region II of the vessel assembly of FIG. 1 in accordance with one embodiment.

FIG. 2 is an enlarged side view of a region II of vessel assembly 100 of FIG. 1 in accordance with one embodiment. Referring now to FIGS. 1 and 2 together, a distal end 218 of anchor delivery system 104 is aligned with and adjacent aneurysm exclusion stent-graft 102 at a location where an anchor is to be deployed.

As used herein, the proximal end of a prosthesis such as aneurysm exclusion stent-graft 102 is the end closest to the heart via the path of blood flow whereas the distal end is the end furthest away from the heart during deployment. In contrast and of note, the distal end of the delivery system such as anchor delivery system 104 is usually identified to the end that is farthest from the operator (handle) while the proximal end of the delivery system is the end nearest the operator (handle). However, those of skill in the art will understand that depending upon the access location, the stent-graft and delivery system description may be consistent or opposite in actual usage.

Figure 3:
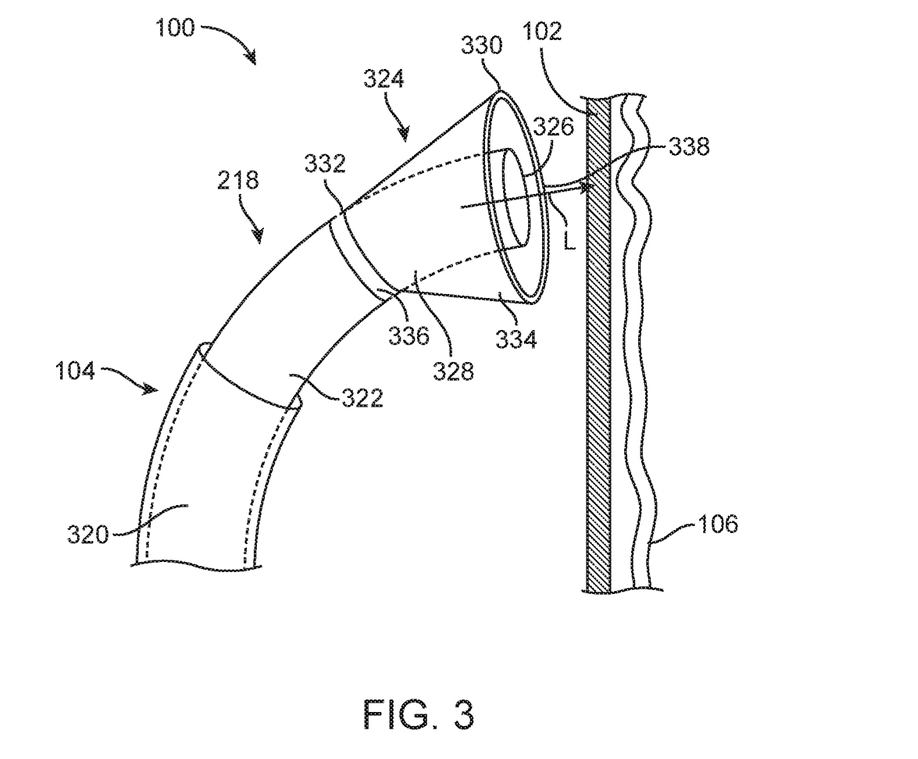
FIG. 3 is an enlarged side view of the region II of the vessel assembly of FIG. 2 at a later stage during deployment of an anchor in accordance with one embodiment.

FIG. 3 is an enlarged side view of the region II of vessel assembly 100 of FIG. 2 at a later stage during deployment of an anchor in accordance with one embodiment. Referring now to FIGS. 1, 2, and 3 together, a delivery sheath 320 is retracted to expose an outer sheath 322 and a conical structure 324 attached to outer sheath 322. Outer sheath 322 includes a distal end 326 and a distal portion 328 at distal end 326.

Conical structure 324 includes a first base 330, a second base 332, and a conical section 334 extending between first base 330 and second base 332. First base 330 and second base 332 are sometimes called a distal end 330 and a proximal end 332, respectively, of conical section 334 and more generally of conical structure 324.

In accordance with this embodiment, conical section 334 is conical. More particularly, conical section 334 is a conical frustum having first base 330 and second base 332. The diameter of conical section 334 in a plane perpendicular to a longitudinal axis L of anchor delivery system 104 increases as the distal distance from second base 332 increases, i.e., between second base 332 and first base 330. Conical structure 324, and more particularly second base 332, is coupled to distal portion 328 of outer sheath 322 by an attachment means 336, e.g., by stitching, adhesive, or other attachment means. First base 330 is coplanar with distal end 326 of outer sheath 322.

To allow visualization of conical structure 324, conical structure 324 is partially or completely radiopaque. In one embodiment, conical section 334 includes radiopaque fabric, a radiopaque marker, or other radiopaque material. Alternatively, or in addition, conical structure 324 includes a radiopaque expansion member 338, sometimes called a radiopaque hoop, at first base 330.

In accordance with one embodiment, expansion member 338 includes a resilient ring, e.g., a metallic ring, stent ring, or other self-expanding structure, at first base 330. Expansion member 338 is configured to expand upon deployment to thereby open conical structure 324.

More particularly, delivery sheath 320 constrains conical structure 324 and expansion member 338 in a delivery profile, sometimes called a closed or crimped state, as illustrated in FIG. 2. As illustrated in FIG. 3, delivery sheath 320 is retracted to expose conical structure 324 and expansion member 338. Upon being exposed and unrestrained, expansion member 338 expands thus increasing the diameter to expansion member 338 and opening conical structure 324 to be in an open state. In accordance with this embodiment, expansion member 338 is spaced apart from aneurysm exclusion stent-graft 102 to insure conical structure 324 fully opens.

Figure 4:
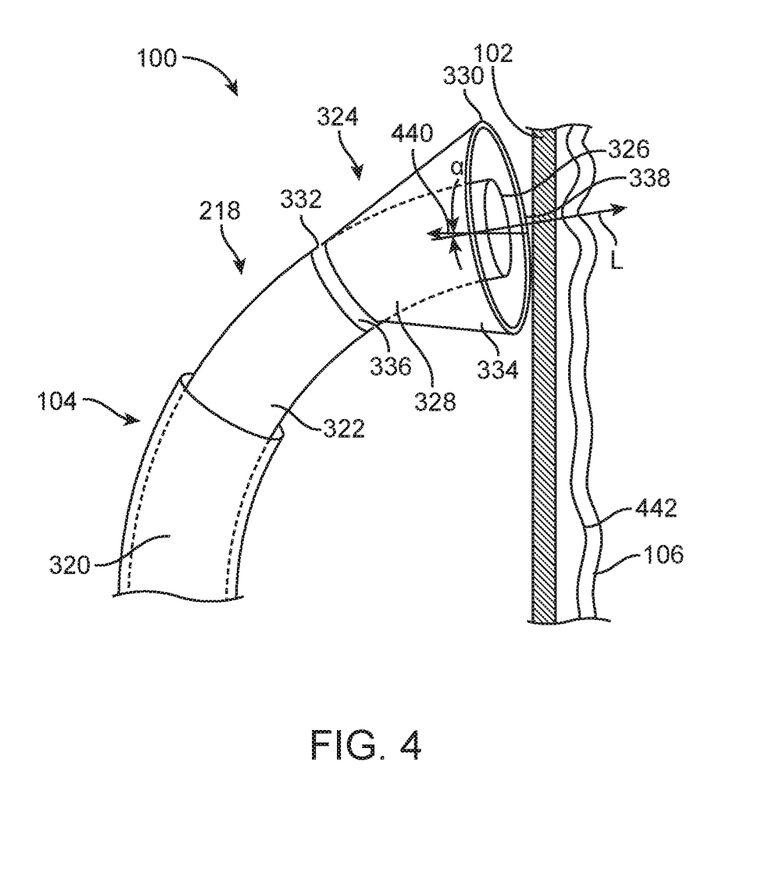
FIG. 4 is an enlarged side view of the region II of the vessel assembly of FIG. 3 at a later stage during deployment of an anchor in accordance with one embodiment.

FIG. 4 is an enlarged side view of the region II of vessel assembly 100 of FIG. 3 at a later stage during deployment of an anchor in accordance with one embodiment. Referring now to FIGS. 3 and 4 together, after retraction of delivery sheath 320 and deployment of conical structure 324 to be in an open state as illustrated in FIG. 3, anchor delivery system 104 including conical structure 324 is advanced to make contact with aneurysm exclusion stent-graft 102 as illustrated in FIG. 4.

In another embodiment, anchor delivery system 104 is moved into contact with aneurysm exclusion stent-graft 102 and then delivery sheath 320 is withdrawn. In accordance with this embodiment, conical structure 324 is deployed into the open state while being in contact with aneurysm exclusion stent-graft 102. Accordingly, the operation of advancing conical structure 324 after deployment into the open state to make contact with aneurysm exclusion stent-graft 102 is optional. For example, flow moves directly from the view of FIG. 2 to the view of FIG. 4.

Paying particular attention now to FIG. 4, the longitudinal axis L of anchor delivery system 104 may be offset relative to the normal direction 440 of aneurysm exclusion stent-graft 102. Longitudinal axis L is the axis of anchor delivery system 104 and is normal to a plane defined by expansion member 338 in one embodiment. Normal direction 440 is a direction perpendicular (normal) to aneurysm exclusion stent-graft 102 at the location where the anchor is being deployed.

More particularly, an angle α may exist between longitudinal axis L and normal direction 440, angle α being greater than zero degrees (0°). Stated another way, anchor delivery system 104 may not be normal to aneurysm exclusion stent-graft 102 and a vessel wall 442 of primary vessel 106. As set forth above, conical structure 324 is radiopaque or includes radiopaque markers to show the location and orientation of the anchor prior to deployment.

Figure 5:
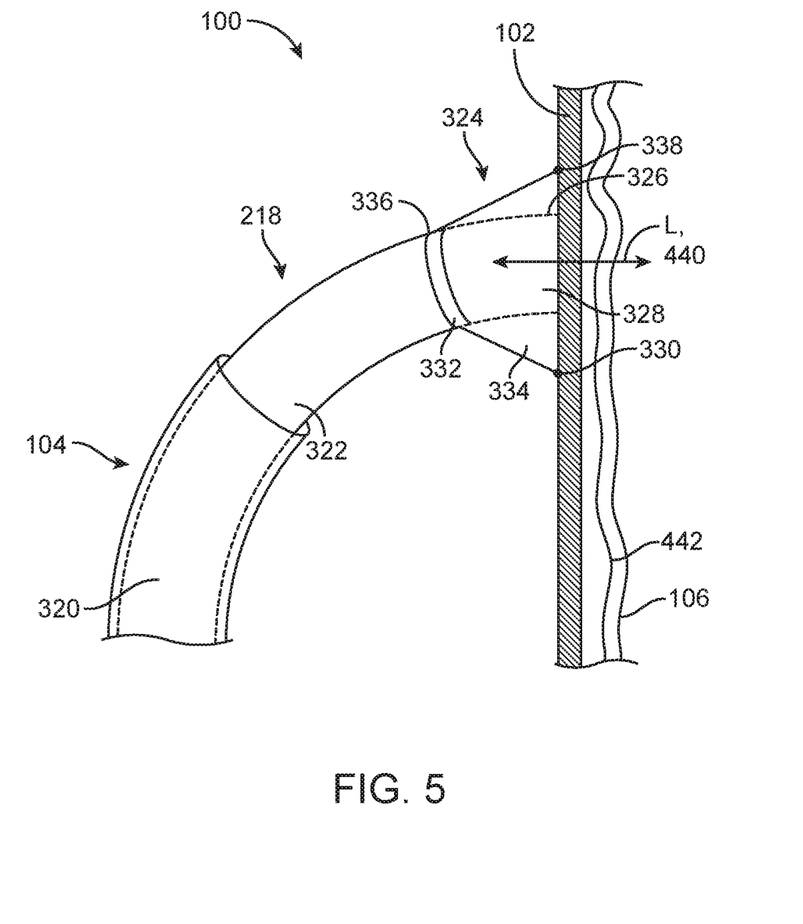
FIG. 5 is an enlarged side view of the region II of the vessel assembly of FIG. 4 at a later stage during deployment of an anchor in accordance with one embodiment.

FIG. 5 is an enlarged side view of the region II of vessel assembly 100 of FIG. 4 at a later stage during deployment of an anchor in accordance with one embodiment. Referring now to FIGS. 4 and 5 together, further advancement of conical structure 324 presses conical structure 324 against aneurysm exclusion stent-graft 102 and vessel wall 442. Conical structure 324 has sufficient rigidity to resist buckling such that first base 330 is pressed to be flush against aneurysm exclusion stent-graft 102 and vessel wall 442.

In other words, conical structure 324 is pressed against aneurysm exclusion stent-graft 102 and vessel wall 442 to cause longitudinal axis L to become normal to aneurysm exclusion stent-graft 102 and vessel wall 442. The larger diameter of conical structure 324 (than the diameter of outer sheath 322) is pushed against the target aiding in holding anchor delivery system 104, sometimes called the catheter, orthogonal to the target. Thus, longitudinal axis L become parallel to normal direction 440. Although the terms parallel, perpendicular, and similar terms are used herein to describe the relationship of various features, in light of this disclosure, those of skill in the art will understand that the features may not be exactly parallel or perpendicular, but only substantially parallel or perpendicular, e.g., to within accepted tolerances. Generally, angle α in FIG. 4 is reduced in FIG. 5, ideally to zero degrees (0°).

Figure 6:
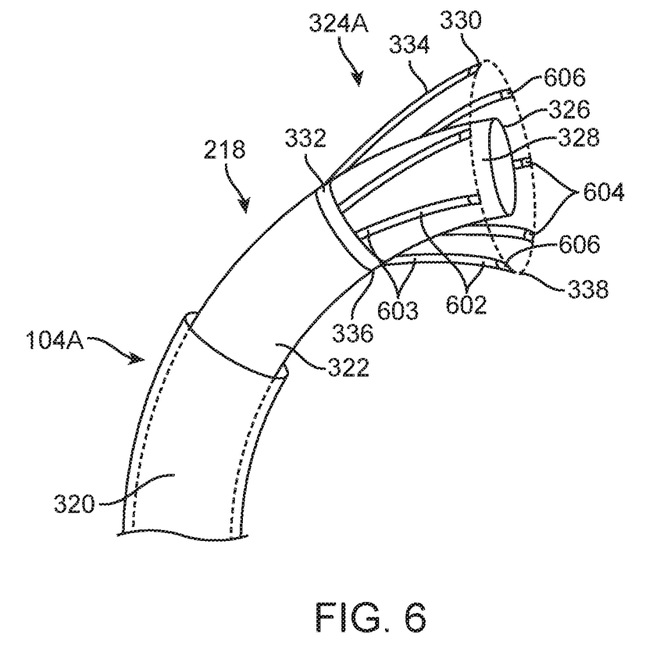
FIG. 6 is a perspective view of an anchor delivery system in accordance with another embodiment.

FIG. 6 is a perspective view of an anchor delivery system 104A in accordance with another embodiment. Anchor delivery system 104A of FIG. 6 is similar to anchor delivery system 104 of FIGS. 1-5 and only the significant differences between anchor delivery system 104A and anchor delivery system 104 are discussed below.

Referring now to FIG. 6, in accordance with this embodiment, a conical structure 324A includes a plurality of individual spars 602. Spars 602 are resilient self-expanding members in accordance with one embodiment, e.g., nitinol, stainless steel, or other material. Upon retraction of delivery sheath 320, spars 602 self-expand and open first base 330.

Spars 602 include first ends 603, sometime called proximal ends 603, coupled to distal portion 328 of outer sheath 322 and second ends 604, sometimes called distal ends 604.

In accordance with this embodiment, conical section 334 is non-continuous and is defined by spars 602. Further, the distal ends 604 of spars 602 define first base 330. First base 330 is also non-continuous in one embodiment.

In one embodiment, distal ends 604 include radiopaque markers 606 to allow visualization of conical structure 324A. In another embodiment, an expansion member 338 or other radiopaque structure is coupled to distal ends 604 of spars 602. Conical structure 324A insures that anchor delivery system 104A is normal to aneurysm exclusion stent-graft 102 and vessel wall 442 in a similar manner to anchor delivery system 104 as described above in reference to FIGS. 1-5, so the description is not repeated here.

FIG. 7 is a cross-section view of distal end 218 of anchor delivery system 104 of FIGS. 1-5 in accordance with one embodiment. In FIG. 7, delivery sheath 320 and conical structure 324 are not illustrated for simplicity. Anchor delivery system 104 includes an anchor 704, an inner member 706, a middle member 708, and outer sheath 322.

Figure 8:
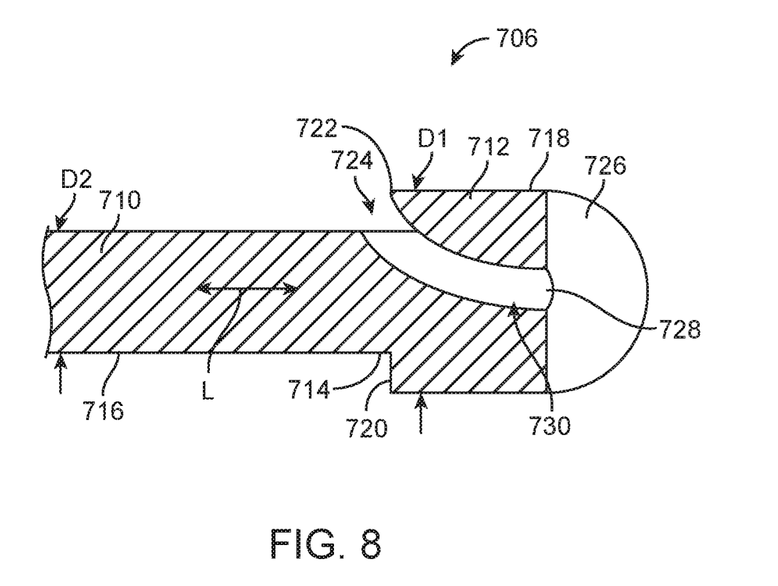
FIG. 8 is a cross-section view of an inner member of the delivery system of FIG. 7 in accordance with one embodiment.
Figure 9:
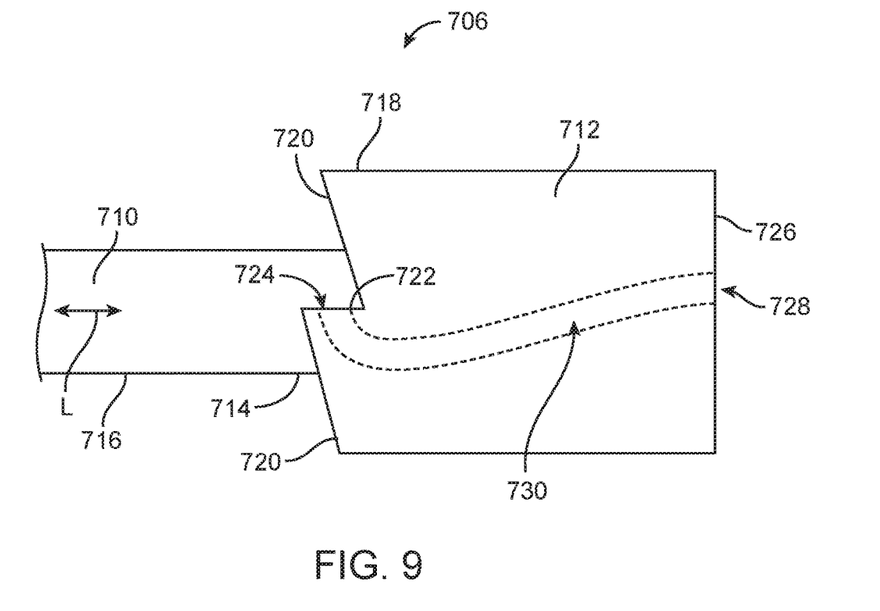
FIG. 9 is a top plan view of the inner member of FIG. 8 in accordance with one embodiment.

FIG. 8 is a cross-section view of inner member 706 of delivery system 104 of FIG. 7 in accordance with one embodiment. FIG. 9 is a top plan view of inner member 706 of FIG. 8 in accordance with one embodiment. Referring now to FIGS. 7, 8, and 9 together, inner member 706 include a main shaft 710 and an anchor guide tip 712. Anchor guide tip 712 is on a distal end 714 of main shaft 710. Although not illustrated, in one embodiment, inner member 706 includes one or more lumens, e.g., guidewire lumens, allowing anchor delivery system 104 to be advanced over a guidewire.

Main shaft 710 is cylindrical in accordance with the embodiment, e.g., includes a cylindrical outer surface 716. Anchor guide tip 712 is also cylindrical, e.g., includes a cylindrical outer surface 718. A diameter D1 of anchor guide tip 712 is greater than a diameter D2 of main shaft 710 such that a proximal surface 720 of inner member tip 712 is defined. Proximal surface 720 extends radially outward from main shaft 710 and perpendicular to longitudinal axis L although can be slanted and/or have other configurations. In one embodiment, proximal surface 720 is helical, sometimes called spiral. Illustratively, a pitch of proximal surface 720 is approximately equal to a pitch of anchor 704.

Anchor guide tip 712 further includes an entrance port surface 722 having an entrance port 724 therein. In one embodiment, entrance port surface 722 is a surface extending radially from outer surface 716 of main shaft 710 and in a direction parallel to longitudinal axis L although can be slanted and/or have other configurations in other embodiments. Entrance port 724 is generally at a proximal end of anchor guide tip 712.

Anchor guide tip 712 further includes a distal surface 726 having an exit port 728 therein. In one embodiment, exit port 728 is in the center of distal surface 726 such that distal surface 726 is a circular annulus. However, in other embodiments, exit port 728 is offset from the center of distal surface 726, e.g., to allow easier loading of anchor 704. Generally, entrance port 724 is radially outward of exit port 728 from longitudinal axis L of anchor guide tip 712.

An anchor guide lumen 730 extends between entrance port 724 and exit port 728. Generally, anchor guide lumen 730 extends from main shaft 710 through anchor guide tip 712 to distal surface 726 of anchor guide tip 712. Anchor guide lumen 730 is a curved lumen extending from a direction perpendicular to entrance port surface 722 to a direction perpendicular to distal surface 726. Cylindrical outer surface 718 of anchor guide tip 712 extends between distal surface 726 and proximal surface 720/entrance port surface 722.

Anchor 704 is located around main shaft 710, extends into entrance port 724, through anchor guide lumen 730 to exit or be adjacent to exit port 728. In its relaxed and undeformed state, anchor 704 is a helical anchor having a pointed, sometimes called sharp, distal tip 732. Anchor 704 is advanced by being rotated by middle member 708.

Figure 10:
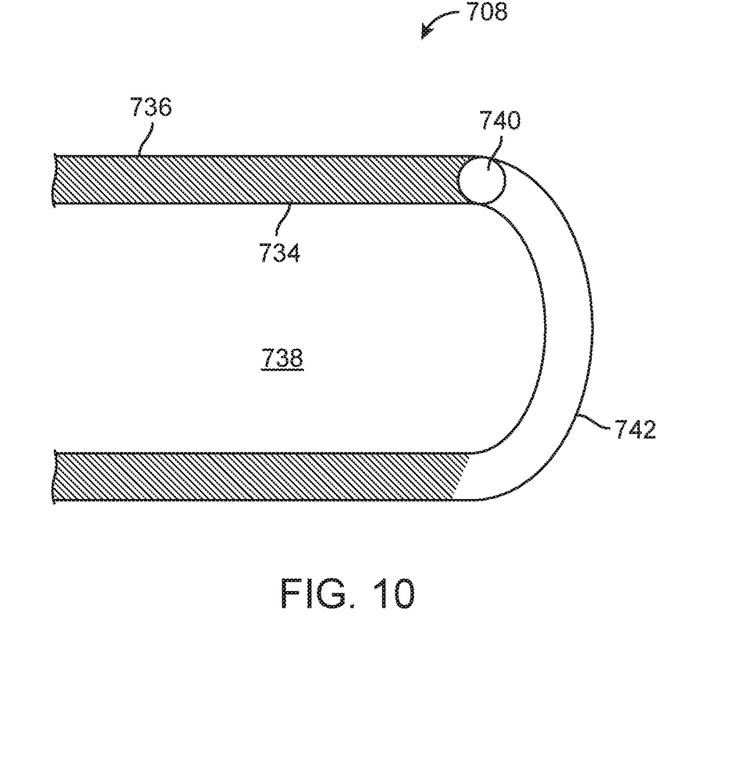
FIG. 10 is a cross-sectional view of the middle member of the delivery system of FIG. 7 in accordance with one embodiment.
Figure 11:
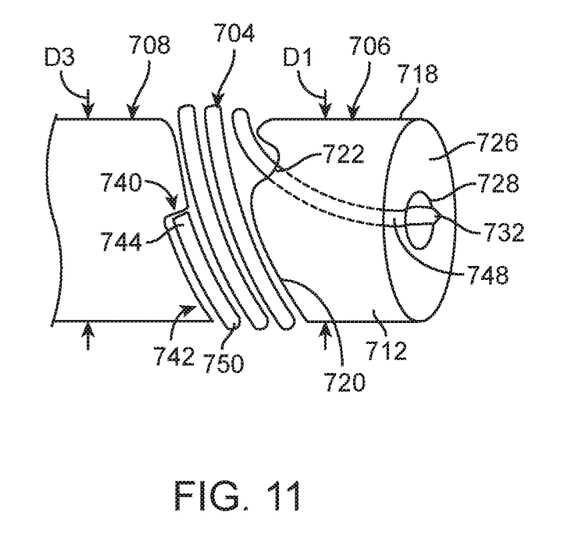
FIG. 11 is a side perspective view of an anchor, the inner member, and a middle member of the delivery system of FIG. 7 in accordance with one embodiment.

FIG. 10 is a cross-sectional view of middle member 708 of delivery system 104 of FIG. 7 in accordance with one embodiment. FIG. 11 is a side perspective view of anchor 704, inner member 706, and middle member 708 of delivery system 104 of FIG. 7 in accordance with one embodiment. Referring now to FIGS. 7-11 together, middle member 708 is a hollow cylinder in accordance with this embodiment and include a cylindrical inner surface 734 and a cylindrical outer surface 736. Middle member 708 includes a middle member lumen 738 in which inner member 706, i.e., main shaft 710, is disposed.

Middle member 708 includes an anchor driving seat 740, e.g., a surface, at a distal end 742 of middle member 708. Anchor driving seat 740 extends from inner surface 734 to outer surface 736 in one embodiment. In one embodiment, anchor driving seat 740 is a surface extending radially outward and in a direction parallel to longitudinal axis L although can be slanted and/or have other configurations in other embodiments.

Anchor driving seat 740 is configured to engage anchor 704, e.g., the proximal end 744 of anchor 704. Anchor 704 is located around main shaft 710 and between middle member 708 and anchor guide tip 712.

Middle member 708 is rotated relative to inner member 706 to cause anchor 704 also to rotated relative to inner member 706. Rotation of anchor 704 causes tip 732 of anchor 704 to enter into entrance port 724, pass through anchor guide lumen 730 and exit through exit port 728. Generally, rotation of middle member 708 advances anchor 704 through anchor guide lumen 730.

Outer sheath 322 is a hollow cylinder in accordance with this embodiment and includes a lumen 746 in which middle member 708, anchor 704, and inner member 706 are disposed. Diameter D1 of anchor guide tip 712 is equal to diameter D3 of middle member 708 in one embodiment such that outer sheath 322 is directly adjacent both middle member 708 and anchor guide tip 712.

FIG. 12 is a partial cross-sectional view of anchor 704 during deployment in accordance with one embodiment. Referring to FIGS. 1, 7-12 together, in its relaxed and undeformed state, anchor 704 is a helical coil, e.g., a tightly coiled nitinol wire structure. Tip 732 lies along the helix of anchor 704 when anchor 704 is in its relaxed state.

During deployment, anchor 704 is superelastically deformed by being passed through anchor guide lumen 730. More particularly, a distal portion 748 of anchor 704 is superelastically deformed such that tip 732, and more generally distal portion 748, of anchor 704 longitudinally protrude, i.e., in longitudinal direction L. As used herein, superelastically deformed means being capable of returning to its original form, sometimes called relaxed (undeformed) state, after being deformed. In one embodiment, anchor 704 is made of a shape memory material such as nickel titanium alloy, sometimes called nitinol.

The longitudinally protruding distal portion 748 including tip 732 is longitudinally advanced to cause tip 732 to exit from exit port 728 in a longitudinal direction parallel to longitudinal axis L. This causes tip 732 to be forced into and pierce aneurysm exclusion stent-graft 102 and vessel wall 442 in normal direction 440. By causing tip 732 to penetrate straight-on to aneurysm exclusion stent-graft 102 and vessel wall 442, the force required to cause anchor 704 to pass through aneurysm exclusion stent-graft 102 and vessel wall 442 is minimized. Stated another way, by causing tip 732 to protrude longitudinally during deployment, it is easier to penetrate aneurysm exclusion stent-graft 102 and vessel wall 442 than if tip 732 were deployed at an angle. This is because the locating and support forces are in direct opposition of the piercing whereas a screw in motion creates forces not easily resolved by the delivery catheter. Further, accuracy in the location of penetration of aneurysm exclusion stent-graft 102 and vessel wall 442 by anchor 704 is maximized.

FIG. 13 is a partial cross-sectional view of the final deployed state of anchor 704 in accordance with one embodiment. As shown in FIG. 13, after passing through aneurysm exclusion stent-graft 102 and vessel wall 442, distal portion 748 of anchor 704 returns to its relaxed state. It should be understood that the entire anchor 704 is passed through anchor guide lumen 730 but returns to its relaxed state. In its final deployed state, a proximal portion 750 of anchor 704 is adjacent aneurysm exclusion stent-graft 102 and distal portion 748 is adjacent vessel wall 442. By having anchor 704 return to its relaxed state where tip 732 lies along the helix of anchor 704, better clamping of aneurysm exclusion stent-graft 102 to vessel wall 442 by anchor 704 is achieved.

More particularly, in accordance with one embodiment, a tightly coiled nitinol wire structure is used as anchor 704. Anchor 704 is superelastically deflected by anchor guide tip 712 to gain a desired attach angle for piercing/engagement. Anchor 704 recovers to its initial shape to lock in place/hold the pierced items together.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A delivery system comprising:
    an inner member comprising:
        a main shaft; and
        an anchor guide tip at a distal end of the main shaft, wherein the anchor guide tip comprises an anchor guide lumen extending from the main shaft through the anchor guide tip to a distal surface of the anchor guide tip; and
    a helical anchor around the main shaft and within the anchor guide lumen, a distal portion of the helical anchor being superelastically deformed by the anchor guide lumen to be parallel to a longitudinal axis of the anchor guide tip.

2. The delivery system of claim 1 wherein the anchor guide lumen extends from an entrance port at a proximal end of the anchor guide tip to an exit port in the distal surface of the anchor guide tip.

3. The delivery system of claim 2 wherein the entrance port is radially outward of the exit port from the longitudinal axis of the anchor guide tip.

4. The delivery system of claim 2 wherein the exit port is at a center of the distal surface of the anchor guide tip.

5. The delivery system of claim 4 wherein the distal surface comprises a circular annulus.

6. The delivery system of claim 1 wherein a diameter of the anchor guide tip is greater than a diameter of the main shaft.

7. The delivery system of claim 1 further comprising:
    a middle member comprising an inner member lumen, the inner member being disposed in the inner member lumen.

8. The delivery system of claim 7 wherein the middle member comprises an anchor driving seat at a distal end of the middle member.

9. The delivery system of claim 8 wherein the anchor driving seat extends from an inner surface of the middle member to an outer surface of the middle member.

10. The delivery system of claim 9 wherein a diameter of the outer surface of the middle member is equal to a diameter of the anchor guide tip.

11. The delivery system of claim 7 further comprising an outer sheath comprising a lumen, the inner member and the middle member being within the lumen of the outer sheath.

12. The delivery system of claim 1 further comprising:
    an outer sheath comprising a distal portion at a distal end of the outer sheath; and
    a conical structure coupled to the distal portion of the outer sheath, the conical structure comprising a conical frustum comprising a first base and a second base, the first base being coplanar with the distal end of the outer sheath, the second base being coupled to the distal portion of the outer sheath.

13. The delivery system of claim 12 wherein the conical structure is radiopaque.

14. The delivery system of claim 12 wherein the conical structure comprises a plurality of spars having first ends coupled to the distal portion of the outer sheath and second ends defining the first base of the conical structure.

15. The delivery system of claim 14 wherein the conical structure further comprises a radiopaque hoop coupled to the second ends.

16. The delivery system of claim 12 wherein the first base defines a distal end of the conical structure and the second base defines a proximal end of the conical structure.

17. The delivery system of claim 1,
    wherein the main shaft comprises a cylindrical outer surface, and
    wherein the anchor guide tip comprises a cylindrical outer surface having a diameter greater than a diameter of the cylindrical outer surface of the main shaft, the anchor guide tip further comprising a proximal surface extending outward from the cylindrical outer surface of the main shaft to the cylindrical outer surface of the anchor guide tip.

18. The delivery system of claim 17 wherein the proximal surface is helical.

19. The delivery system of claim 17 where the anchor guide tip further comprises an entrance port surface extending outward from the cylindrical outer surface of the main shaft, an entrance port of the anchor guide lumen being within the entrance port surface.

20. The delivery system of claim 1 wherein the helical anchor comprises a pointed distal tip.

* * * * *